(12) United States Patent
Giles

(10) Patent No.: US 7,829,849 B2
(45) Date of Patent: Nov. 9, 2010

(54) MASS SPECTROMETER

(75) Inventor: Kevin Giles, Cheshire (GB)

(73) Assignee: Micromass UK Ltd., Manchester (GB)

( * ) Notice: Subject to any disclaimer, the term of this patent is extended or adjusted under 35 U.S.C. 154(b) by 441 days.

(21) Appl. No.: 11/816,221

(22) PCT Filed: Feb. 14, 2006

(86) PCT No.: PCT/GB2006/000504

§ 371 (c)(1),
(2), (4) Date: May 23, 2008

(87) PCT Pub. No.: WO2006/085110

PCT Pub. Date: Aug. 17, 2006

(65) Prior Publication Data

US 2009/0057546 A1 Mar. 5, 2009

Related U.S. Application Data

(60) Provisional application No. 60/657,792, filed on Mar. 2, 2005.

(30) Foreign Application Priority Data

Feb. 14, 2005 (GB) ................................ 0503010.1

(51) Int. Cl.
H01J 49/00 (2006.01)

(52) U.S. Cl. ........................ 250/290; 250/281; 250/282; 250/283; 250/286; 250/287; 250/288; 250/289; 250/291; 250/292; 250/293

(58) Field of Classification Search ......... 250/281–283, 250/286–293

See application file for complete search history.

(56) References Cited

U.S. PATENT DOCUMENTS

| 2003/0057367 A1 | 3/2003 | Guevremont et al. |
| 2003/0150985 A1* | 8/2003 | Guevremont et al. ....... 250/287 |
| 2009/0173880 A1* | 7/2009 | Bateman et al. ............. 250/292 |

FOREIGN PATENT DOCUMENTS

GB 2392005 2/2004

* cited by examiner

*Primary Examiner*—Jack I Berman
*Assistant Examiner*—Meenakshi S Sahu
(74) *Attorney, Agent, or Firm*—Jamie H. Rose

(57) ABSTRACT

A device (6) for separating ions according to differences in their ion mobility as a function of electric field strength is disclosed. The device (6) comprises an upper electrode (7a), a lower electrode (7b) and a plurality of intermediate electrodes (8). An asymmetric voltage waveform is applied to the upper electrode (7a) and a DC compensating voltage is applied to the lower electrode (7b).

22 Claims, 8 Drawing Sheets

MASS SPECTROMETER

CROSS REFERENCE TO RELATED APPLICATIONS

This application is the National Stage of International Application No. PCT/GB2006/000504, filed on Feb. 14, 2005, which claims priority to and benefit of U.S. Provisional Patent Application Ser. No. 60/657,792 filed on Mar. 2, 2005, and priority to and benefit of United Kingdom Patent Application No. 0503010.1, filed Feb. 14, 2005. The entire contents of these applications are incorporated herein by reference.

The present invention relates to a device for separating ions according to differences in their ion mobility as a function of electric field strength. The present invention also relates to a mass spectrometer, a method of separating ions according to differences in their ion mobility as a function of electric field strength and a method of mass spectrometry. The preferred embodiment relates to an asymmetric electric field ion mobility separator or spectrometer comprising a stacked array of electrodes. Ions are retained within the device by the application of an AC or RF voltage to the stacked array of electrodes.

The mobility K of an ion in a gas under the influence of an electric field E can be considered as being independent of the applied electric field under conditions wherein the energy gained by the ion from the electric field is negligible compared with thermal energies. Such conditions are met when the ratio of the strength of the applied electric field E to the neutral gas number density N of the gas is relatively low. However, if the strength of the electric field is increased or if the neutral gas number density is decreased then the mobility of an ion may then be observed as being dependent upon the ratio of the electric field strength to the neutral gas number density E/N. The mobility of the ion is observed as having a dependence as follows:

$$K\left(\frac{E}{N}\right) = K_0\left[1 + \alpha\left(\frac{E}{N}\right)\right] \quad (1)$$

wherein $K_0$ is the mobility of the ion when the ratio E/N is relatively low and $\alpha(E/N)$ is a function representing the dependence of the mobility of the ion as the strength of the applied electric field increases.

A knowledge of the dependence of the mobility of an ion with electric field strength prompted development of the first differential ion mobility analyser by Buryakov et al. as disclosed in International Journal of Mass Spectrometry and Ion Processes 128 (1993) pp 143-148. The differential ion mobility analyser developed by Buryakov operated by separating ions according to differences in the mobilities of ions under low and high strength electric fields.

The device developed by Buryakov et al. is shown schematically in FIGS. 1A and 1B. The device comprised a pair of parallel electrodes 2a,2b. A flow of gas 5 was arranged to pass between the two electrodes 2a,2b and ions which were to be separated were arranged to be entrained in the flow of gas 5. An asymmetric potential difference or voltage waveform 3 was arranged to be maintained between the electrodes 2a,2b.

The asymmetric potential difference or voltage waveform 3 which was applied to the electrodes is shown in FIG. 2 and comprised a relatively high positive voltage $V_{high}$ for a relatively short period of time $T_{high}$ followed by a relatively low negative voltage $V_{low}$ for a relatively long period of time $T_{low}$. The asymmetric potential difference or voltage waveform 3 was arranged such that the product $V_{high} \times T_{high}$ equalled the product $V_{low} \times T_{low}$. Consequently, if the mobility of an ion when the electric field was relatively low was the same when the electric field was relatively high then the average trajectory of the ion through the device could be expected to remain substantially parallel to the electrodes 2a,2b. The ion would therefore be expected to be onwardly transmitted through the device as shown in FIG. 1A.

If the mobility of the ion varied with electric field strength then the ion would then be expected to drift towards one or other of the electrodes 2a;2b. The ion would therefore ultimately become lost to the system by hitting one of the electrodes 2a;2b. This is shown in FIG. 1B. However, by applying a DC compensation voltage 4 to one of the electrodes 2a;2b the drift of the ion towards one of the electrodes 2a;2b can be compensated for. By appropriate setting of the DC compensation voltage 4 it is possible to arrange for ions having a specific ion mobility to be onwardly transmitted by the device whereas other ions will drift towards one of the electrodes 2a,2b and will become lost to the system.

Known differential ion mobility analysers do not confine ions within the analyser and therefore operate at atmospheric pressure since at atmospheric pressures the rate of ion diffusion is lower than at sub-atmospheric pressures. Accordingly, the loss of ions as they pass through the ion mobility analyser is minimized. If the gas pressure were to be reduced to sub-atmospheric pressures then ion diffusion would then become an important loss mechanism and the ion mobility analyser would suffer from unacceptable losses of ions.

A disadvantage of known ion mobility analysers is that since they need to operate at atmospheric pressures then high voltage RF generators are also required in order to provide an asymmetric waveform which has a high enough peak amplitude in order to be able to generate an asymmetric voltage waveform which can enable high-field mobility effects to be observed.

It is therefore desired to provide an improved ion mobility analyser.

According to an aspect of the present invention there is provided a device comprising:
one or more first electrodes;
one or more second electrodes;
one or more layers of intermediate electrodes arranged generally or substantially in a plane in which ions travel in use, the one or more layers of intermediate electrodes being arranged between the one or more first electrodes and the one or more second electrodes; and
first voltage means arranged and adapted to apply an asymmetric voltage waveform to the one or more first electrodes and/or to the one or more layers of intermediate electrodes and/or to the one or more second electrodes.

The device is preferably selected from the group consisting of: (i) a high field asymmetric waveform ion mobility separator or spectrometer; (ii) an ion mobility separator or spectrometer; (iii) a gas phase electrophoresis device; (iv) a differential ion mobility separator, spectrometer or device; (v) a Field Asymmetric Ion Mobility Spectrometry ("FAIMS") device; (vi) a gas phase ion separator or spectrometer; (vii) a device for separating ions according to their mobility; and (viii) a device for separating ions according to differences or changes of their ion mobility with electric field strength.

The asymmetric voltage waveform preferably comprises at least a first voltage component $V_{high}$ having a first peak amplitude and at least a second voltage component $V_{low}$ having a second peak amplitude, wherein the first peak amplitude is substantially different to the second peak amplitude. The first peak amplitude may be positive or negative and/or the second peak amplitude may be positive or negative. The first peak amplitude and/or the second peak amplitude are preferably selected from the group consisting of: (i) less than −1000 V; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to −90 V; (xi) −90 to −80 V; (xii) −80 to −70 V; (xiii) −70 to −60 V; (xiv) −60 to −50 V; (xv) −50 to −40 V; (xvi) −40 to −30 V; (xvii) −30 to −20 V; (xviii) −20 to −10 V; (xix) −10 to 0 V; (xx) 0 to 10 V; (xxi) 10 to 20 V; (xxii) 20 to 30 V; (xxiii) 30 to 40 V; (xiv) 40 to 50 V; (xxv) 50 to 60 V; (xxvi) 60 to 70 V; (xxvii) 70 to 80 V; (xxviii) 80 to 90 V; (xxix) 90 to 100 V; (xxx) 100 to 200 V; (xxxi) 200 to 300 V; (xxxii) 300 to 400 V; (xxxiii) 400 to 500 V; (xxxiv) 500 to 600 V; (xxxv) 600 to 700 V; (xxxvi) 700 to 800 V; (xxxvii) 800 to 900 V; (xxxviii) 900 to 1000 V; and (xxxix) more than 1000 V.

The first voltage component is preferably applied or present for a first time period $T_{high}$ and wherein the second voltage component is applied or present for a second time period $T_{low}$. The first time period $T_{high}$ may be shorter, longer or substantially the same as the second time period $T_{low}$.

The first time period $T_{high}$ and/or the second time period $T_{low}$ are preferably selected from the group consisting of: (i) <0.1 μs; (ii) 0.1-0.5 μs; (iii) 0.5-1 μs; (iv) 1-2 μs; (v) 2-3 μs; (vi) 3-4 μs; (vii) 4-5 μs; (viii) 5-6 μs; (ix) 6-7 μs; (x) 7-8 μs; (xi) 8-9 μs; (xii) 9-10 μs; (xiii) 10-11 μs; (xiv) 11-12 μs; (xv) 12-13 μs; (xvi) 13-14 μs; (xvii) 14-15 μs; (xviii) 15-16 μs; (xix) 16-17 μs; (xx) 17-18 μs; (xxi) 18-19 μs; (xxii) 19-20 μs; and (xxiii) >20 μs.

According to an embodiment the asymmetric voltage waveform comprises a waveform selected from the group consisting of: (i) rectangular; (ii) non-rectangular; (iii) curved; (iv) regular; (v) irregular; (vi) stepped; (vii) sawtooth; and (viii) sinusoidal.

According to the preferred embodiment the device preferably comprises second voltage means arranged and adapted to apply a DC compensation voltage to the one or more first electrodes and/or to the one or more layers of intermediate electrodes and/or to the one or more second electrodes. The DC compensation voltage is preferably selected from the group consisting of: (i) less than −1000 V; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to −90 V; (xi) −90 to −80 V; (xii) −80 to −70 V; (xiii) −70 to −60 V; (xiv) −60 to −50 V; (xv) −50 to −40 V; (xvi) −40 to −30 V; (xvii) −30 to −20 V; (xviii) −20 to −10 V; (xix) −10 to 0 V; (xx) 0 to 10 V; (xxi) 10 to 20 V; (xxii) 20 to 30 V; (xxiii) 30 to 40 V; (xiv) 40 to 50 V; (xxv) 50 to 60 V; (xxvi) 60 to 70 V; (xxvii) 70 to 80 V; (xxviii) 80 to 90 V; (xxix) 90 to 100 V; (xxx) 100 to 200 V; (xxxi) 200 to 300 V; (xxxii) 300 to 400 V; (xxxiii) 400 to 500 V; (xxxiv) 500 to 600 V; (xxxv) 600 to 700 V; (xxxvi) 700 to 800 V; (xxxvii) 800 to 900 V; (xxxviii) 900 to 1000 V; and (xxxix) more than 1000 V.

In a mode of operation the second voltage means is preferably arranged and adapted to sweep, vary, progressively vary or switch the DC compensation voltage applied to the one or more first electrodes and/or to the one or more layers of intermediate electrodes and/or to the one or more second electrodes. The second voltage means may be arranged and adapted to sweep, vary, progressively vary or switch the DC compensation voltage in a generally or substantially stepped, linear, regular, irregular, periodic or non-periodic manner.

The device preferably further comprises means arranged so as to provide a stream of gas which flows, in use, through the device and wherein at least some ions are arranged to be onwardly transmitted axially through the device by being entrained in the stream of gas.

According to the preferred embodiment the one or more first electrodes comprises a first array of electrodes. The first array of electrodes preferably comprise at least 2, 3, 4, 5, 6, 7, 8, 9, 10, 11, 12, 13, 14, 15, 16, 17, 18, 19, 20 or more than 20 electrodes.

The device preferably further comprises further voltage means arranged and adapted to apply one or more voltages or potentials or one or more voltage or potential waveforms to the first array of electrodes in order to urge, propel, force or accelerate at least some ions through and/or along at least a portion of the axial length of the device.

The further voltage means is preferably arranged and adapted to apply one or more transient DC voltages or potentials or one or more transient DC voltage or potential waveforms to the first array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The further voltage means may be arranged and adapted to apply one or more substantially constant DC voltages or potentials to the first array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The further voltage means may be arranged and adapted to apply two or more phase-shifted AC or RF voltages to the first array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 859%, 90%, 95% or 100% of the axial length of the device.

The first array of electrodes may comprise: (i) a printed circuit board, printed wiring board or etched wiring board; (ii) a plurality of conductive traces applied or laminated onto a non-conductive substrate; (iii) a plurality of copper or metallic electrodes arranged on a substrate; (iv) a screen printed, photoengraved, etched or milled printed circuit board; (v) a plurality of electrodes arranged on a paper substrate impregnated with phenolic resin; (vi) a plurality of electrodes arranged on a fibreglass mat impregnated within an epoxy resin; (vii) a plurality of electrodes arranged on a plastic substrate; or (viii) a plurality of electrodes arranged on a substrate.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the first electrodes have an axial centre to centre spacing selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the first electrodes have an axial length selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the first electrodes have a width selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

The first electrodes preferably have a thickness selected from the group consisting of: (i) <0.01 mm; (ii) 0.01-0.1 mm; (iii) 0.1-0.2 mm; (iv) 0.2-0.3 mm; (v) 0.3-0.4 mm; (vi) 0.4-0.5 mm; (vii) 0.5-0.6 mm; (viii) 0.6-0.7 mm; (ix) 0.7-0.8 mm; (x) 0.8-0.9 mm; (xi) 0.9-1.0 mm; (xii) 1-2 mm; (xiii) 2-3 mm; (xiv) 3-4 mm; (xv) 4-5 mm; and (xvi) >5 mm.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the first electrodes are biased, in use, at a first bias DC voltage or potential with respect to the mean or average voltage or potential of at least some or all of the intermediate electrodes. The first DC bias voltage or potential is preferably selected from the group consisting of: (i) less than −10V; (ii) −9 to −8V; (iii) −8 to −7V; (iv) −7 to −6V; (v) −6 to −5V; (vi) −5 to −4V; (vii) −4 to −3V; (viii) −3 to −2V; (ix) −2 to −1V; (x) −1 to 0V; (xi) 0 to 1V; (xii) 1 to 2V; (xiii) 2 to 3V; (xiv) 3 to 4V; (xv) 4 to 5V; (xvi) 5 to 6V; (xvii) 6 to 7V; (xviii) 7 to 8V; (xix) 8 to 9V; (xx) 9 to 10V; and (xxi) more than 10V.

The one or more first electrodes may be supplied in a mode of operation with either: (i) a DC only voltage; (ii) an AC or RF only voltage; or (iii) a DC voltage and an AC or RF voltage.

The one or more second electrodes preferably comprise a second array of second electrodes. The second array of electrodes preferably comprises at least 2, 3, 4, 5, 6, 7, 8, 9, 10, 11, 12, 13, 14, 15, 16, 17, 18, 19, 20 or more than 20 electrodes.

According to the preferred embodiment the device preferably further comprises further voltage means arranged and adapted to apply one or more voltages or potentials or one or more voltage or potential waveforms to the second array of electrodes in order to urge, propel, force or accelerate at least some ions through and/or along at least a portion of the axial length of the device.

The further voltage means is arranged and adapted to apply one or more transient DC voltages or potentials or one or more transient DC voltage or potential waveforms to the second array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

According to an embodiment the further voltage means is arranged and adapted to apply one or more substantially constant DC voltages or potentials to the second array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

According to an embodiment the further voltage means is arranged and adapted to apply two or more phase-shifted AC or RF voltages to the second array of electrodes in order to urge, propel, force or accelerate at least some ions through and/or along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second array of electrodes preferably comprises: (i) a printed circuit board, printed wiring board or etched wiring board; (ii) a plurality of conductive traces applied or laminated onto a non-conductive substrate; (iii) a plurality of copper or metallic electrodes arranged on a substrate; (iv) a screen printed, photoengraved, etched or milled printed circuit board; (v) a plurality of electrodes arranged on a paper substrate impregnated with phenolic resin; (vi) a plurality of electrodes arranged on a fibreglass mat impregnated within an epoxy resin; (vii) a plurality of electrodes arranged on a plastic substrate; or (viii) a plurality of electrodes arranged on a substrate.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the second electrodes have an axial centre to centre spacing selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the second electrodes have an axial length selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the second electrodes have a width selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

The second electrodes preferably have a thickness selected from the group consisting of: (i) <0.01 mm; (ii) 0.01-0.1 mm; (iii) 0.1-0.2 mm; (iv) 0.2-0.3 mm; (v) 0.3-0.4 mm; (vi) 0.4-0.5 mm; (vii) 0.5-0.6 mm; (viii) 0.6-0.7 mm; (ix) 0.7-0.8 mm; (x) 0.8-0.9 mm; (xi) 0.9-1.0 mm; (xii) 1-2 mm; (xiii) 2-3 mm; (xiv) 3-4 mm; (xv) 4-5 mm; and (xvi) >5 mm.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the second electrodes are biased, in use, at a second bias DC voltage or potential with respect to the mean or average voltage or potential of at least some or all of the intermediate electrodes. The second DC bias voltage or potential is preferably selected from the group consisting of: (i) less than −10V; (ii) −9 to −8V; (iii) −8 to −7V; (iv) −7 to −6V; (v) −6 to −5V; (vi) −5 to −4V; (vii) −4 to −3V; (viii) −3 to −2V; (ix) −2 to −1V; (x) −1 to 0V; (xi) 0 to 1V; (xii) 1 to 2V; (xiii) 2 to 3V; (xiv) 3 to 4V; (xv) 4 to 5V; (xvi) 5 to 6V; (xvii) 6 to 7V; (xviii) 7 to 8V; (xix) 8 to 9V; (xx) 9 to 10V; and (xxi) more than 10V.

The one or more second electrodes are preferably supplied in a mode of operation with either: (i) a DC only voltage; (ii) an AC or RF only voltage; or (iii) a DC and an AC or RF voltage.

The one or more layers of intermediate electrodes preferably comprise one or more layers of planar, plate or mesh electrodes. Each layer of intermediate electrodes preferably comprises one, two or more than two longitudinal electrodes.

At least some or all of the longitudinal electrodes preferably have a centre to centre separation in a width direction of the device selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

At least some or all of the longitudinal electrodes preferably have an axial length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; and (xxi) >200 mm.

At least some or all of the longitudinal electrodes preferably have a width selected from the group consisting of: (i) <1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

Preferably, at least some or all of the longitudinal electrodes have a thickness selected from the group consisting of: (i) <0.01 mm; (ii) 0.01-0.1 mm; (iii) 0.1-0.2 mm; (iv) 0.2-0.3 mm; (v) 0.3-0.4 mm; (vi) 0.4-0.5 mm; (vii) 0.5-0.6 mm; (viii) 0.6-0.7 mm; (ix) 0.7-0.8 mm; (x) 0.8-0.9 mm; (xi) 0.9-1.0 mm; (xii) 1-2 mm; (xiii) 2-3 mm; (xiv) 3-4 mm; (xv) 4-5 mm; and (xvi) >5 mm.

The two or more longitudinal electrodes in a layer are preferably substantially co-planar. The two or more longitudinal electrodes in a layer are preferably supplied, in use, with substantially the same phase of a two-phase or multi-phase AC or RF voltage or signal.

Adjacent or neighbouring layers of longitudinal electrodes are preferably supplied, in use, with substantially opposite or different phases of a two-phase or multi-phase AC or RF voltage or signal.

The AC or RF voltage or signal supplied, in use, to the longitudinal electrodes preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The amplitude of the AC or RF voltage or signal preferably supplied, in use, to the longitudinal electrodes is selected from the group consisting of: (i) <50V peak to peak; (ii) 50-100V peak to peak; (iii) 100-150V peak to peak; (iv) 150-200V peak to peak; (v) 200-250V peak to peak; (vi) 250-300V peak to peak; (vii) 300-350V peak to peak; (viii) 350-400V peak to peak; (ix) 400-450V peak to peak; (x) 450-500V peak to peak; and (xi) >500V peak to peak.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the intermediate electrodes are supplied with an AC or RF voltage or signal.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are arranged substantially parallel to one another.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are substantially planar or flat and the device curves in the plane of the electrodes.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are substantially non-planar or non-flat such that the electrodes curve along their axial length.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are arranged substantially equidistant from one another.

Preferably, at least 5%, 10%, 15%, 20%, 25%, 30%, 35%, 40%, 45%, 50%, 55%, 60%, 65%, 70%, 75%, 80%, 85%, 90%, 95% or 100% of the layers of intermediate electrodes are spaced apart from one another by a distance selected from the group consisting of: (i) less than or equal to 5 mm; (ii) less than or equal to 4.5 mm; (iii) less than or equal to 4 mm; (iv) less than or equal to 3.5 mm; (v) less than or equal to 3 mm; (vi) less than or equal to 2.5 mm; (vii) less than or equal to 2 mm; (viii) less than or equal to 1.5 mm; (ix) less than or equal to 1 mm; (x) less than or equal to 0.8 mm; (xi) less than or equal to 0.6 mm; (xii) less than or equal to 0.4 mm; (xiii) less than or equal to 0.2 mm; (xiv) less than or equal to 0.1 mm; and (xv) less than or equal to 0.25 mm.

The device preferably has either a substantially linear, non-linear, regular, non-regular or curved ion guiding region.

The device may have an entrance for receiving ions along a first axis and an exit from which ions emerge from the device along a second axis, wherein the second axis makes an angle θ to the first axis, and wherein θ falls within the range selected from the group consisting of: (i) <100; (ii) 10-20°; (iii) 20-30°; (iv) 30-40°; (v) 40-50°; (vi) 50-60°; (vii) 60-70°; (viii) 70-80°; (ix) 80-90°; (x) 90-100°; (xi) 100-110°; (xii) 110-120°; (xiii) 120-130°; (xiv) 130-140°; (xv) 140-150°; (xvi) 150-160°; (xvii) 160-170°; (xviii) 170-180°; and (xix) 180°.

The device preferably comprises an ion guiding region arranged between an ion entrance of the device and an ion exit of the device, and wherein the ion guiding region is substantially linear, non-linear, regular, non-regular, curved, "S"-shaped or has one, two or more than two points of inflexion.

The device may have one, two, three or more than three separate entrances for receiving ions and one, two, three or more than three separate exits from which ions may emerge from the device.

The device preferably has an entrance having a first cross-sectional profile and a first cross-sectional area and an exit having a second cross-sectional profile and a second cross-sectional area. The first cross-sectional profile may be different to the second cross-sectional profile and/or the first cross-sectional area may be different to the second cross-sectional area.

The first cross-sectional profile and/or the second cross-sectional profile may have a substantially circular, oval, rectangular or square cross-section.

The device may be arranged and adapted to be coupled to an ion-optical component selected from the group consisting of: (i) an ion-optical component having a substantially circular, square, rectangular or elliptical cross-sectional profile; (ii) a quadrupole mass filter/analyser having a substantially circular or elliptical cross-sectional profile; (iii) an orthogonal acceleration Time of Flight mass analyser having a substantially square or rectangular cross-sectional profile; (iv) a magnetic sector analyser having a substantially rectangular cross-sectional profile; (v) a Fourier Transform Ion Cyclotron Resonance ("FTICR") mass analyser having a substantially circular or elliptical cross-sectional profile; (vi) a 2D (linear) quadrupole ion trap having a substantially circular or elliptical cross-sectional profile; and (vii) a 3D (Paul) quadrupole ion trap having a substantially circular or elliptical cross-sectional profile.

The device may comprise an ion guiding region arranged between an entrance and an exit, and wherein the ion guiding region either: (i) varies in size and/or shape along the length of the ion guiding region; or (ii) has a width and/or height which progressively tapers or enlarges in size.

The device is preferably maintained, in use, at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) >100 mbar; (viii) >1000 mbar; (ix) 0.0001-0.001 mbar; (x) 0.001-0.01 mbar; (xi) 0.01-0.1 mbar; (xii) 0.1-1 mbar; (xiii) 1-10 mbar; (xiv) 10-100 mbar; and (xv) 100-1000 mbar.

The device is preferably maintained, in use, at a pressure selected from the group consisting of: (i) <0.0001 mbar; (ii) <0.001 mbar; (iii) <0.01 mbar; (iv) <0.1 mbar; (v) <1 mbar; (vi) <10 mbar; (vii) <100 mbar; and (viii) <1000 mbar.

The device may be arranged and adapted to receive a substantially continuous beam of ions and is arranged and adapted to release or eject ions as a plurality of packets or bunches of ions.

The device may be arranged and adapted to convert a substantially continuous beam of ions into a pulsed or discontinuous beam of ions.

In a mode of operation the device may be arranged to operate as an ion guide and to onwardly transmit ions without separating ions according to their mobility.

In a mode of operation the device may be arranged to operate as a collision, fragmentation or reaction device.

The collision, fragmentation or reaction device may comprise a Collision Induced Dissociation ("CID") collision or fragmentation device.

The collision, fragmentation or reaction device may be selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The device preferably further comprises a plurality of insulator layers interspersed or interleaved between the one or more layers of intermediate electrodes.

At least 5%, 10%, 15%, 20%, 25%, 30%, 35%, 40%, 45%, 50%, 55%, 60%, 65%, 70%, 75%, 80%, 85%, 90%, 95% or 100% of the one or more layers of intermediate electrodes are preferably arranged on or are deposited on the insulator layers.

According to another aspect of the present invention there is provided a mass spectrometer comprising one or more devices as described above.

The mass spectrometer preferably further comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The ion source may comprise a pulsed or continuous ion source.

The mass spectrometer preferably further comprises a mass analyser arranged downstream of the device. The mass analyser is preferably selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an axial acceleration Time of Flight mass analyser; and (xiv) an orthogonal acceleration Time of Flight mass analyser.

The mass spectrometer preferably further comprises one or more mass or mass to charge ratio filters and/or mass analysers arranged upstream and/or downstream of the device. The one or more mass or mass to charge ratio filters and/or mass analysers are preferably selected from the group consisting of: (i) a quadrupole mass filter or analyser; (ii) a Wien filter; (iii) a magnetic sector mass filter or analyser; (iv) a velocity filter; (v) an ion gate; and (vi) an orthogonal acceleration Time of Flight mass analyser.

According to another aspect of the present invention there is provided a method of separating ions comprising:

providing a device comprising one or more first electrodes, one or more second electrodes and one or more layers of intermediate electrodes arranged generally or substantially in the plane in which ions travel, the one or more layers of intermediate electrodes being arranged between the one or more first electrodes and the one or more second electrodes; and applying an asymmetric voltage waveform to the one or more first electrodes and/or the one or more layers of intermediate electrodes and/or the one or more second electrodes.

According to another aspect of the present invention there is provided a method of mass spectrometry comprising a method of separating ions as described above.

According to another aspect of the present invention there is provided a device comprising:

one or more first electrodes;

one or more second electrodes; and first voltage means arranged and adapted to apply an asymmetric voltage waveform to the one or more first electrodes and/or to the one or more second electrodes;

wherein the device is arranged and adapted to be maintained, in use, at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vii) 1-10 mbar; and (viii) 10-100 mbar.

According to another aspect of the present invention there is provided a mass spectrometer comprising a device as described above.

According to another aspect of the present invention there is provided a method of separating ions comprising:

providing a device comprising one or more first electrodes and one or more second electrodes;

applying an asymmetric voltage waveform to the one or more first electrodes and/or to the one or more second electrodes; and maintaining the device at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vii) 1-10 mbar; and (viii) 10-100 mbar.

According to another aspect of the present invention there is provided a method of mass spectrometry comprising a method as described above.

The preferred embodiment relates to a device wherein an asymmetric voltage waveform is preferably applied to one or more electrodes of the device. The applied asymmetric voltage is arranged preferably to cause ions to be separated according to differences in the mobility of ions under relatively high and low strength electric fields. The preferred device can advantageously be operated at sub-ambient pressures and a relatively low voltage RF generator can be used in order to generate the asymmetric voltage waveform which is preferably applied to at least one of the electrodes.

According to an embodiment the device may be operated at a pressure in the range $10^{-2}$ to 100 mbar. According to a particularly preferred embodiment the device may be operated at a pressure in the range $10^{-1}$ to 10 mbar.

The RF generator may according to an embodiment comprise a relatively low voltage RSF generator which preferably provides a voltage waveform having a maximum or peak amplitude of <100V (or >−100 V).

Ions are preferably radially confined within the preferred device by an inhomogeneous AC or RF electric field. The inhomogeneous AC or RF electric field is preferably achieved by applying an AC or RF voltage to at least some of the intermediate electrodes so that ions are confined radially within the preferred device.

Various embodiments of the present invention together with other arrangements given for illustrative purposes only will now be described, by way of example only, and with reference to the accompanying drawings in which:

FIG. 1A shows the trajectory of an ion through a known differential ion mobility separator if the mobility of the ion is substantially independent of electric field strength and an asymmetric voltage waveform as shown in FIG. 2 is applied to the upper electrode and FIG. 1B shows the trajectory of an ion through the known differential ion mobility separator if the mobility of the ion exhibits a dependence upon the strength of the applied electric field and an asymmetric voltage waveform as shown in FIG. 2 is applied to the upper electrode;

Figure 14:
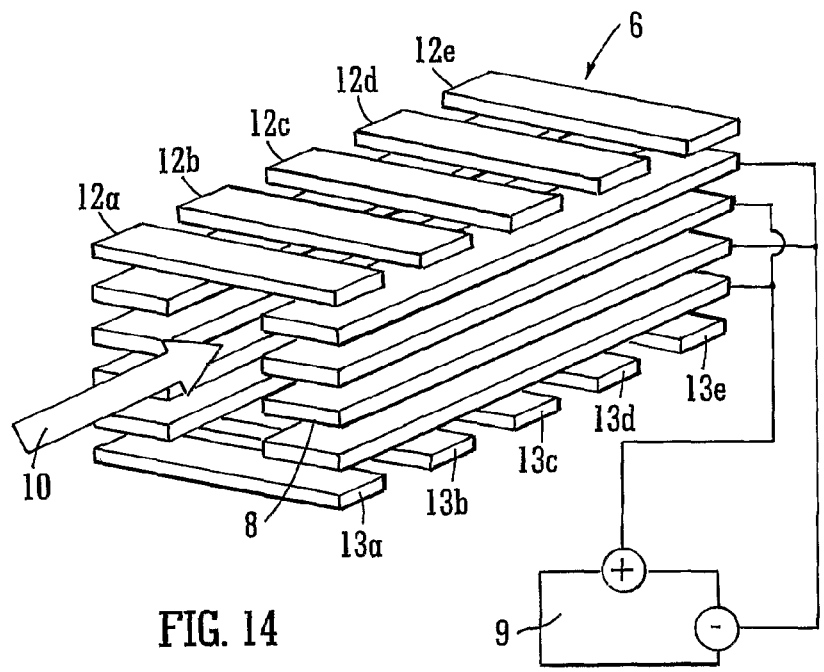
Figure 15:
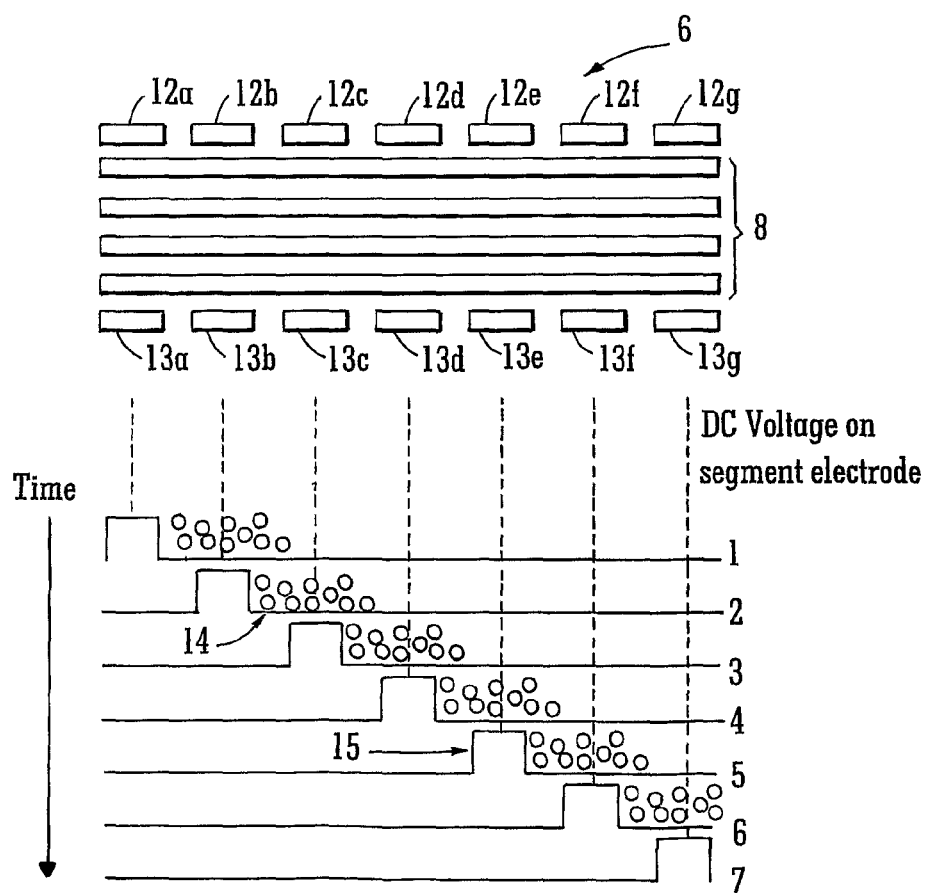

FIG. 14 shows a device according to a preferred embodiment wherein a plurality of axially segmented upper and lower electrodes are provided which enables a voltage gradient or a time varying voltage profile to be maintained along the axial length of the device so that ions may be urged along and through the preferred device; and FIG. 15 shows a transient DC voltage or potential being progressively applied to the axially segmented upper and lower electrodes in order to urge ions along and through the preferred device.

Figure 3:
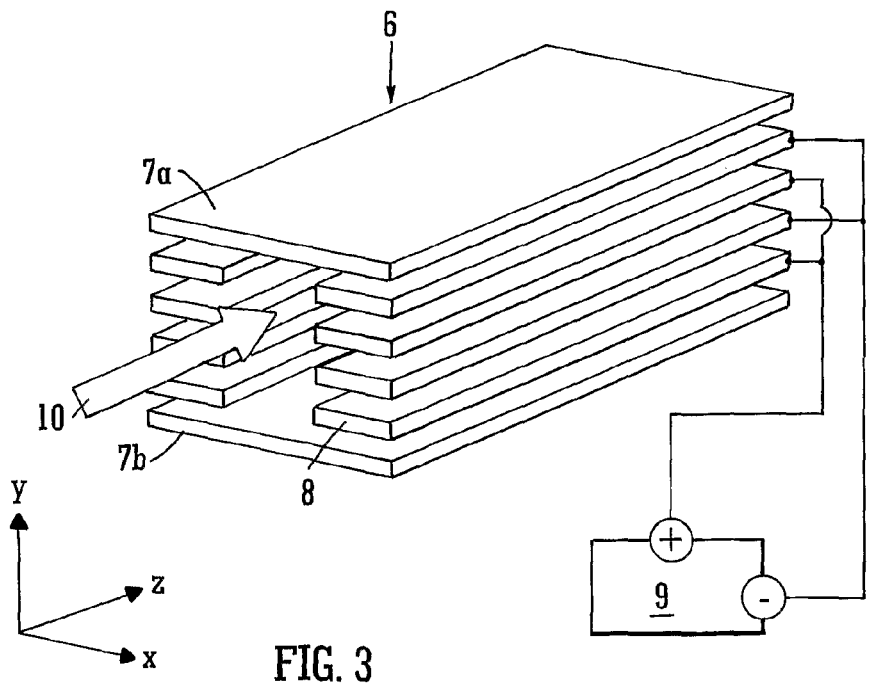
FIG. 3 shows a differential ion mobility separator or spectrometer according to an embodiment of the present invention.

A differential ion mobility separator or spectrometer 6 according to a preferred embodiment of the present invention will now be described with reference to FIG. 3. The differential ion mobility separator or spectrometer 6 preferably comprises an upper electrode 7a, a lower electrode 7b and one or more layers of intermediate electrodes 8. The upper electrode 7a and/or the lower electrode preferably comprise a planar, plate or mesh electrode. The intermediate electrodes 8 are preferably arranged horizontally between the upper electrode 7a and the lower electrode 7b. The intermediate electrodes 8 preferably comprise one or more planar, plate or mesh electrodes. The layers of intermediate electrodes 8 are preferably arranged such that they lie preferably generally or substantially in a plane in which ions travel in use.

According to the preferred embodiment each intermediate layer of electrodes preferably comprises two longitudinal electrodes. The two longitudinal electrodes are preferably horizontally or otherwise separated from each other such that an ion guiding region is preferably provided or formed in between the longitudinal electrodes.

The two longitudinal electrodes in any particular intermediate layer are preferably supplied with the same phase of an AC or RF voltage 9. The longitudinal electrodes in a neighbouring or vertically adjacent intermediate layer are preferably supplied with an opposite phase of the AC or RF voltage 9. The application of an AC or RF voltage 9 to the intermediate or longitudinal electrodes 8 preferably causes ions to be confined in the radial horizontal radial direction (or x-direction) within a pseudo-potential well. The AC or RF voltage 9 which is preferably applied to the intermediate electrodes 8 preferably has a sinusoidal waveform. However, according to other embodiments the AC or RF voltage may have a non-sinusoidal waveform.

According to the preferred embodiment a DC and/or an AC or RF voltage is preferably applied to the upper electrode 7a and/or to the lower electrode 7b in order to confine ions in the vertical radial direction (or y-direction) within the preferred device 6.

Ion motion in the axial direction (or z-direction) is preferably substantially unimpeded or unaffected by the application of an AC or RF voltage to the intermediate electrodes 8 and by the application of a DC and/or AC or RF voltage to the upper and lower electrodes 7a,7b.

The preferred device 6 can be operated in an ion-guiding only mode of operation wherein an AC or RF voltage is applied to the intermediate electrodes and a DC and/or AC or RF voltage is applied to the upper and lower electrodes 7a,7b. When the preferred device 6 is operated in an ion-guiding only mode of operation an asymmetric voltage waveform is not applied to either the upper electrode 7a or the lower electrode 7b.

When the preferred device 6 operates in an ion guiding only mode of operation the device 6 acts as an ion guide and preferably transmits ions either in the presence of a background neutral gas or in the absence of any such gas. The preferred device 6 can advantageously be operated as an ion guide in an ion guiding only mode of operation at sub-ambient pressures whilst minimising diffusive loss.

According to the preferred embodiment the device 6 is preferably operated in a mode of operation wherein the device 6 operates as a differential ion mobility separator or spectrometer. According to this embodiment ions are preferably arranged to be separated within the device 6 as a result of ions having an ion mobility at low electric field strengths which differs from the mobility of the ions at high electric field strengths.

According to the preferred embodiment an asymmetric voltage waveform is preferably applied to either the upper electrode 7a or the lower electrode 7b. According to an embodiment the asymmetric voltage waveform is preferably applied to the upper electrode 7a. Accordingly, an asymmetric potential difference is preferably maintained between the upper electrode 7a and the lower electrode 7b.

Figure 1A:
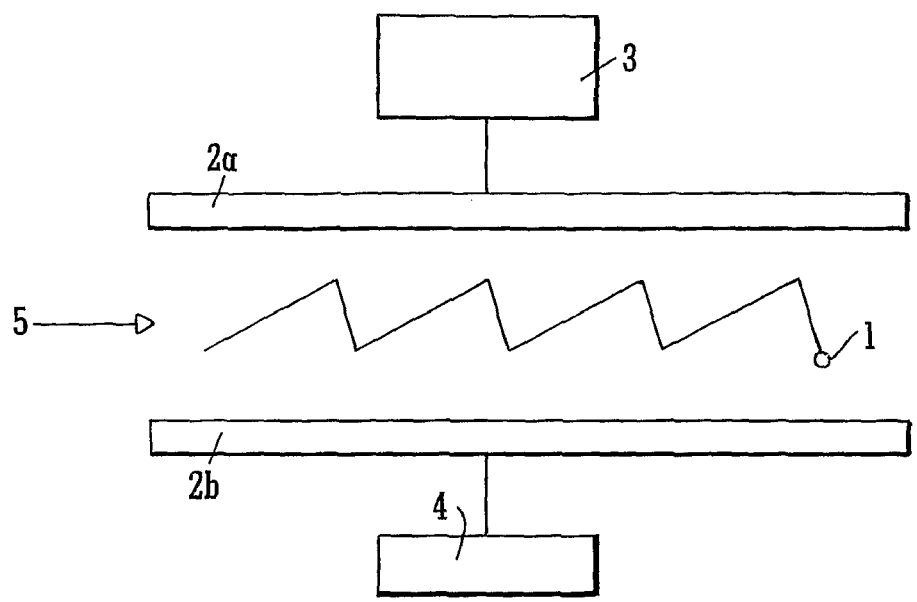
Figure 1B:
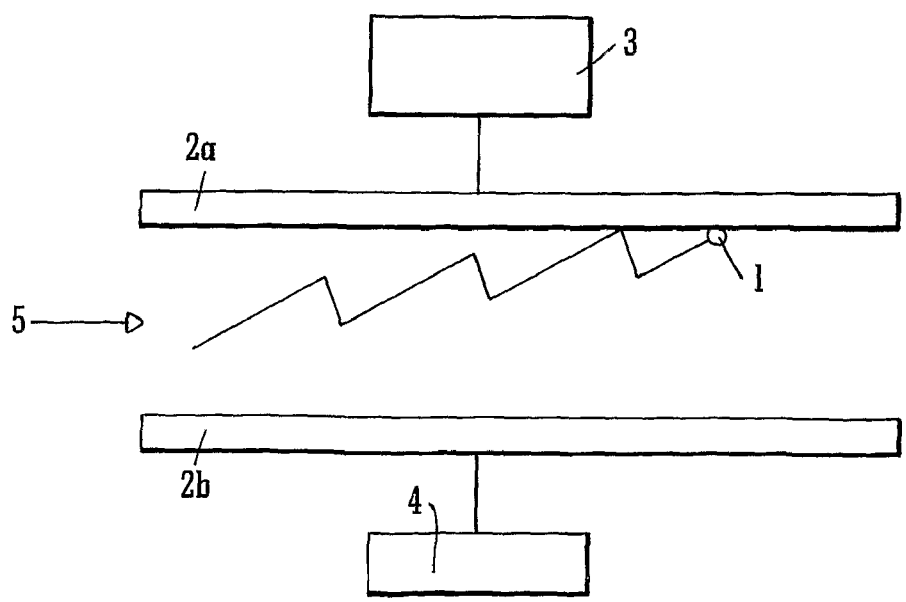
Figure 2:
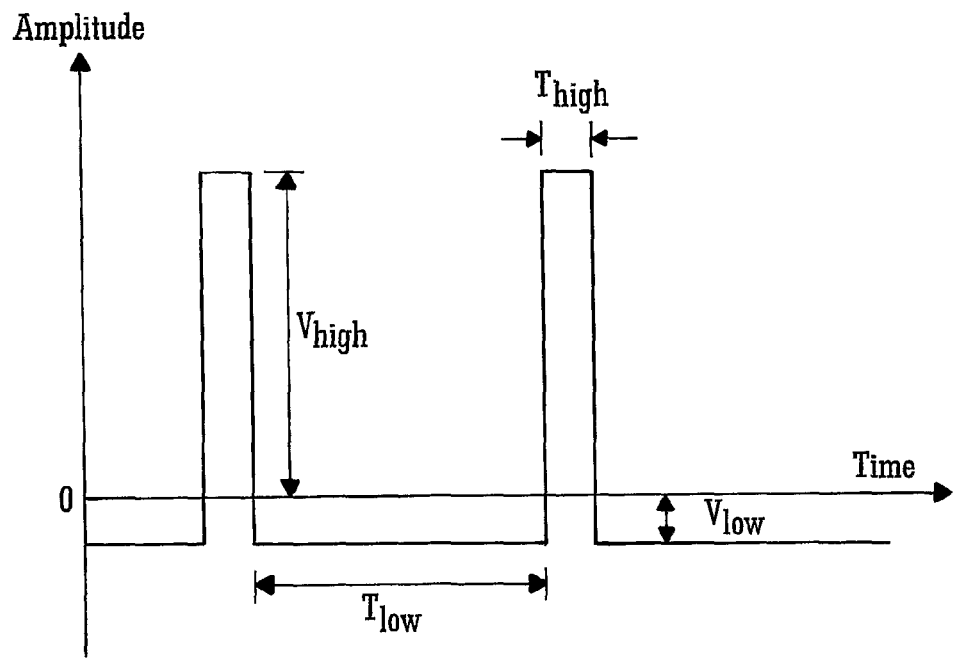
FIG. 2 shows the form of an asymmetric voltage waveform wherein the product $V_{high}*T_{high}$ is arranged to substantially equal the product $V_{low}*T_{low}$.

The asymmetric voltage waveform which is preferably applied to the upper electrode 7a is preferably substantially similar to the asymmetric voltage waveform as shown in FIG. 2 i.e. the product $V_{high}*T_{high}$ is arranged to equal the product $V_{low}*T_{low}$. However, according to other embodiments the asymmetric voltage waveform which is preferably applied to the upper electrode 7a may have a non-rectangular or curved waveform.

The differential ion mobility separator or spectrometer 6 is preferably maintained at sub-ambient gas pressures. Ions are preferably caused to become separated within the device 6 in the vertical radial direction (or y-direction) as the ions pass along and through the preferred device 6. A particular advantage of the preferred device 6 is that the potential or voltage difference between the upper electrode 7a and the lower electrode 7b which is required to be maintained in order to achieve a relatively high ratio of electric field strength E to neutral gas number density N reduces in proportion to the pressure. Therefore, the preferred device 6 can be operated at relatively low pressures but higher order ion mobility effects can nonetheless be observed.

Known differential ion mobility analysers which operate at ambient pressures typically require electric field strengths up to tens of kilovolts per cm in order to separate ions according to differences in the mobility of ions at high and low electric field strengths. However, according to the preferred embodiment the preferred device 6 can be operated at sub-ambient or millibar pressures. As a result the asymmetric voltage waveform which is preferably applied to the device 6 may have a much lower electric field strength in the range of tens of volts per cm. Such a relatively low amplitude voltage waveform is still nonetheless sufficient to be able to cause ions to separate according to differences in their ion mobility under high and low electric fields.

Another advantage of the preferred device 6 is that the voltages which are preferably applied to the upper electrode 7a and/or to the lower electrode 7b and/or to the intermediate electrodes 8 may be changed or altered in a rapid manner. As a result the preferred device 6 may be arranged to change mode of operation effectively instantaneously. The preferred device 6 can therefore be switched from operating in one mode of operation to operating in another mode of operation. For example, the preferred device 6 may be switched from operating in a mode of operation wherein an asymmetric voltage waveform is applied to the upper electrode 7a to then operate in a mode of operation wherein, for example, a symmetric voltage waveform is applied to the upper electrode 7a and/or to the lower electrode 7b.

In a mode of operation instead of applying an asymmetric AC or RF voltage waveform to the upper electrode 7a, a static or DC voltage may instead be applied to the upper electrode 7a and/or to the lower electrode 7b. In this mode of operation the device 6 may then preferably be arranged to operate in an ion guiding of operation wherein ions are preferably arranged to be onwardly transmitted without substantially being separated according to differences in their ion mobility as a function of electric field strength.

According to a yet further embodiment an asymmetric voltage waveform may additionally or alternatively be applied to the longitudinal electrodes or the intermediate electrodes 8. According to this particular embodiment the asymmetric voltage waveform may be arranged so as to be applied to the intermediate electrodes 8 of the device 6 such that the electric field within the device 6 is preferably arranged so as to be substantially constant, uniform or homogenous across at least a portion or substantially the whole of the distance between the upper electrode 7a and the lower electrode 7b at any particular point in time. This is in contrast to the preferred embodiment wherein an inhomogeneous electric field is provided within the device 6 by applying an asymmetric voltage waveform just to the upper electrode 7a.

If a substantially homogenous asymmetric electric field is maintained within the preferred device 6 according to the above described embodiment then the amplitude of the asymmetric voltage waveform which is preferably applied to the longitudinal or intermediate electrodes 8 may be adjusted dependent upon the relative position of the particular electrode between or in relation to the upper electrode 7a and the lower electrode 7b.

Ion motion through the preferred differential ion mobility device 6 in the axial or z-direction direction is preferably perpendicular to the direction of mobility separation which is preferably in the y-direction. Ions are preferably caused to be transmitted through the preferred device by being contained in a flow of neutral gas 10 which is preferably arranged to be passed through the preferred device 6.

Figure 4:
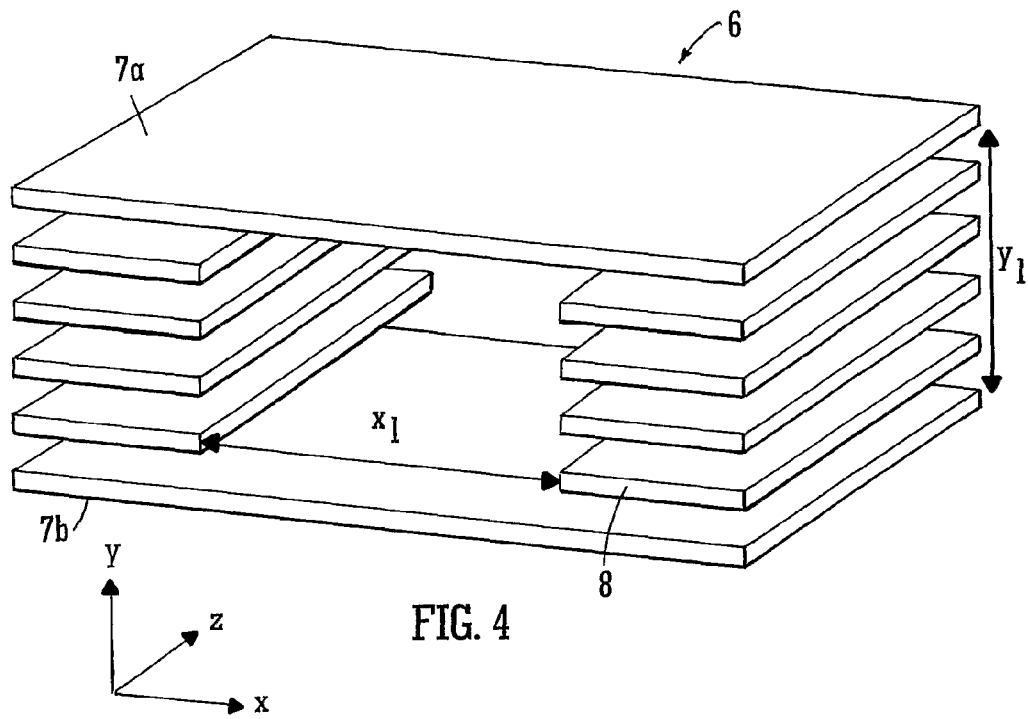
FIG. 4 shows the geometry of a differential ion mobility separator or spectrometer which was used to model the effects of various electric field conditions upon the trajectories of ions passing through the preferred device.

The effect of applying an asymmetric electric field or voltage waveform to the upper electrode 7a in order to cause ions to become separated according to differences in their mobility as a function of electric field strength was modelled using the SIMION® software package. The particular geometry of the differential ion mobility spectrometer or separator 6 which was used to model the trajectories of ions under various different conditions is shown in FIG. 4. The differential ion mobility separator or spectrometer 6 was modelled as comprising an upper electrode 7a, a lower electrode 7b and four intermediate layers of electrodes 8. The four intermediate layers of electrodes 8 were provided in between the upper electrode 7a and the lower electrode 7b. Each intermediate layer of electrodes comprised two longitudinal electrodes. The longitudinal electrodes were longer in the axial or z-direction than the width of the electrodes in the x-direction.

The upper electrode 7a, lower electrode 7b and all of the intermediate electrodes 8 were modelled as being 0.5 mm thick (in the y-direction). The upper electrode 7a, lower electrode 7b and all the intermediate electrodes 8 were also modelled as being arranged such that they had a centre-to-centre spacing of 1.5 mm. The face-to-face spacing $y_1$ between the upper electrode 7a and the lower electrode 7b was arranged to be 7.0 mm. The longitudinal electrodes in each intermediate layer 8 were arranged so as to be separated by a distance $x_1$ of 9.8 mm.

The effect of the dependence of the mobility of an ion with electric field strength as described by Eqn. 1 was incorporated into a user program written into the SIMION® model. Following the approach by Lock and Dyer, both the hard sphere and the Langevin collision cross-sections were calculated at each step of the simulation. The larger of the two collision cross-sections was then used as the interaction cross-section in the collision calculations.

At low electric field strengths the Langevin collision cross section (based upon the ion-induced dipole interaction) is largest but decreases with increasing ion velocity (i.e. increasing electric fields) until it falls below the velocity independent hard sphere collision cross section. The drift velocity of an ion at low electric fields (wherein Langevin effects dominates) is proportional to the electric field E. However, at high electric field strengths the drift velocity is proportional to $E^{0.5}$ (wherein Hard Sphere dominates) resulting in a net drift towards either the upper electrode 7a or the lower electrodes 7b.

Figure 5:
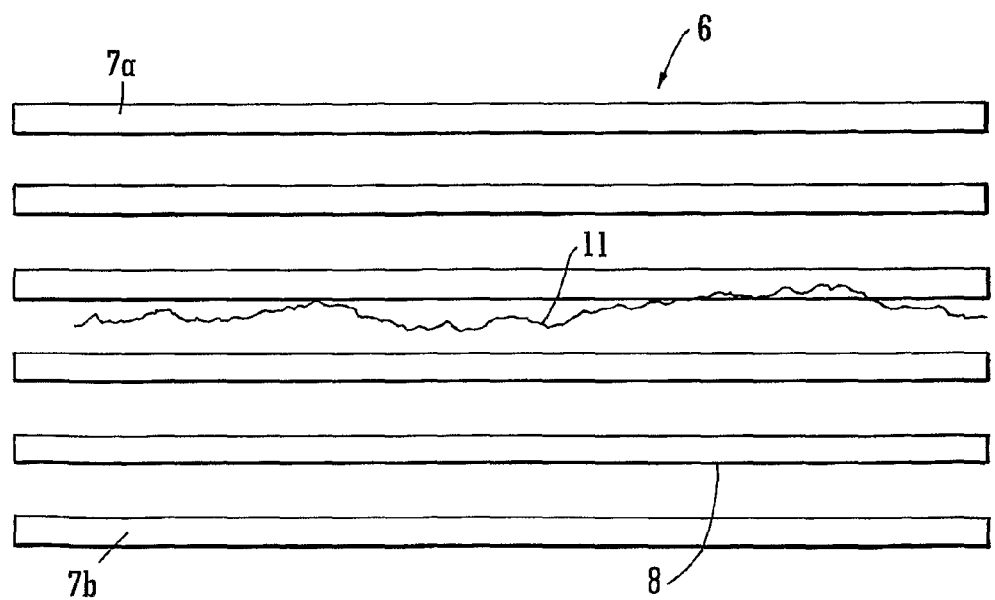
FIG. 5 shows a view of the trajectory of an ion along the length of the preferred device when the device was operated in an ion guiding only mode of operation.

FIG. 5 shows the results of a simulation wherein an ion having a mass to charge ratio of 500 was modelled as passing through the device 6 shown in FIG. 4 but wherein the device 6 was arranged to operate in an ion guiding only mode of operation. According to this mode of operation an asymmetric voltage waveform was not applied to the upper electrode 7a and hence ions were not therefore arranged to be separated according to differences in their ion mobility with electric field strength.

In the various simulations which were performed the intermediate electrodes 8 were modelled as being supplied with an RF voltage having a frequency of 1 MHz and an amplitude of 200 V peak-peak. In the ion guiding only mode of operation the upper electrode 7a and the lower electrode 7b were both modelled as being maintained at 0V DC.

The preferred device 6 was further modelled as being subjected to a simulated gas pressure of 1 mbar of Argon (350 m/s thermal velocity, 1.64 $Å^3$ polarizability). The ion-neutral hard-sphere interaction cross section was modelled as being 200 $Å^2$ and a neutral gas bulk-flow velocity of 50 m/s was assumed.

Figure 6:
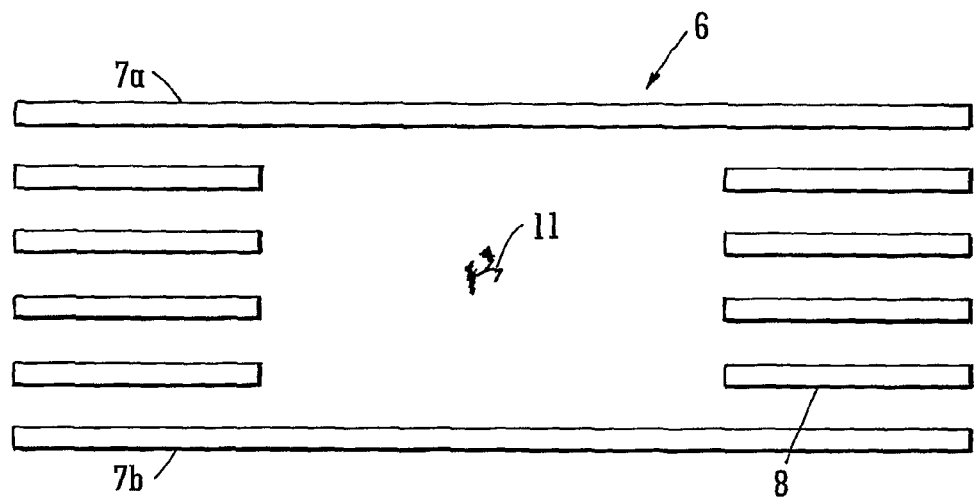
FIG. 6 shows an end-on view of the trajectory of the ion through the preferred device when the device was operated in an ion guiding only mode of operation.

The trajectory 11 of the ion along the axial length of the preferred device 6 operating in the ion guiding only mode of operation is shown in FIG. 5. FIG. 6 shows the trajectory of the same ion looking down the length of the preferred device 6 i.e. looking in the z-direction. As will be appreciated from FIGS. 5 and 6, the ion is effectively transported along and through the length of the preferred device 6.

The effect of applying an asymmetric voltage waveform to the upper electrode 7a was then modelled. A SIMION® user program was used to model the effects of applying an asymmetric voltage waveform to the upper electrode 7a such that a high field voltage of 10*V was modelled as being applied to the upper electrode 7a for a period of time T. A low field voltage of −V was then modelled as being applied to the upper electrode 7a for a period of time 10*T. The lower electrode was meanwhile modelled as being maintained at 0V.

Figure 7:
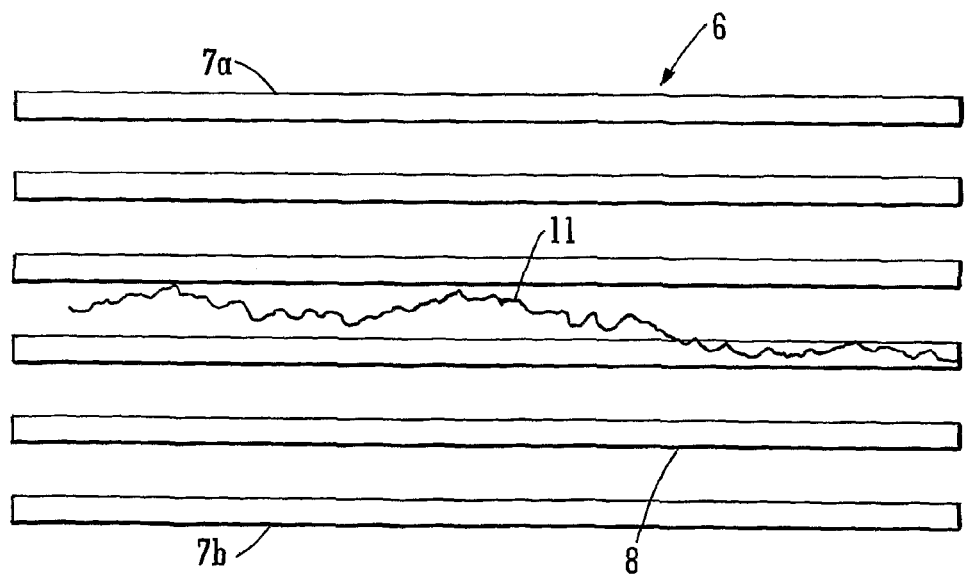
FIG. 7 shows how the trajectory of an ion is only mildly modulated when a relatively low amplitude asymmetric voltage waveform was applied to the upper electrode of the preferred device.

FIG. 7 shows the result of a simulation wherein the parameter V was set to a relatively low value of 1 V and the parameter T was set to 1 μs. Accordingly, a high field voltage of only 10 V was applied to the upper electrode 7a for a time period 1 μs followed by a low field voltage of only −1 V being applied to the upper electrode 7a for a time period 10 μs. The other simulation parameters were kept the same as those used in the simulation described above in relation to FIGS. 5 and 6.

As can be seen from FIG. 7, the application of a relatively low amplitude asymmetric waveform to the upper electrode 7a had the effect of causing only a relatively small or minor degree of modulation to the trajectory 11 of the ion. It is also apparent that no particularly strong deviation of the ion to either the upper electrode 7a or to the lower electrode 7b was observed.

Figure 8:
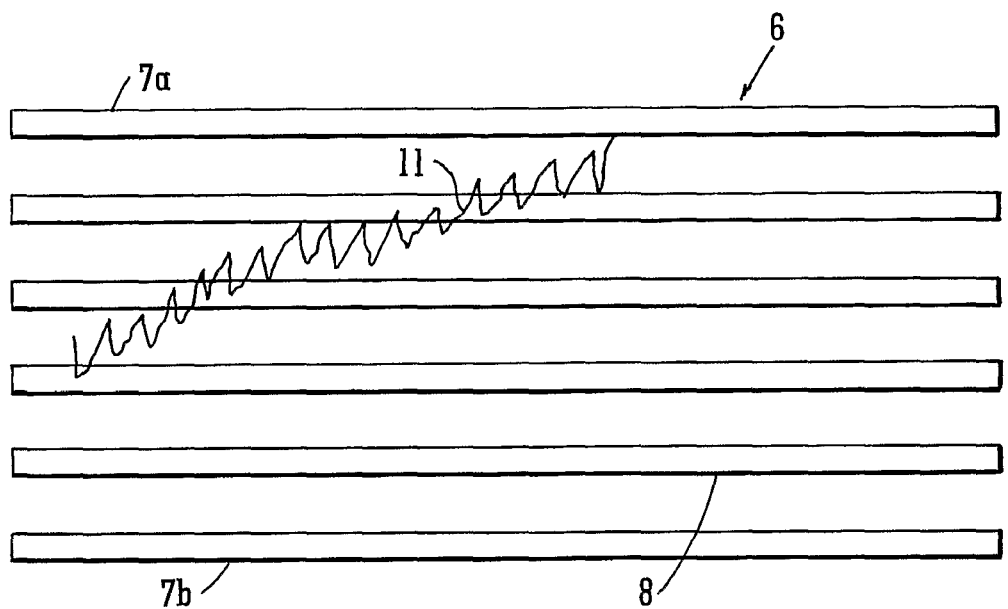
FIG. 8 shows how the trajectory of an ion passing through the preferred device is strongly modulated when a high voltage asymmetric voltage waveform was applied to the upper electrode of the preferred device.

FIG. 8 shows the result of a simulation wherein the voltage was increased such that the parameter V was now increased to 7 V. The parameter T was kept constant at 1 μs. Accordingly, a high field voltage of 70V was applied to the upper electrode 7a for a time period 1 μs and a low field voltage of −7V was applied to the upper electrode 7a for a time period 10 μs. The other simulation parameters were kept the same as were used in respect of the simulation described above in relation to FIG. 7.

As is apparent from FIG. 8, when the amplitude of the asymmetric waveform was increased then a marked drift of the ion towards the upper electrode 7a was observed. This is due to the ion having a comparatively greater ion mobility under low electric field strength conditions (−7V) which meant that the ion is influenced to a greater extent during the longer low electric field portion of the applied asymmetric waveform.

As will now be discussed, the net or resultant drift of an ion towards either the upper electrode 7a or the lower electrode 7b can be compensated for by, for example, applying a compensating DC voltage to the lower electrode 7b.

Figure 9:
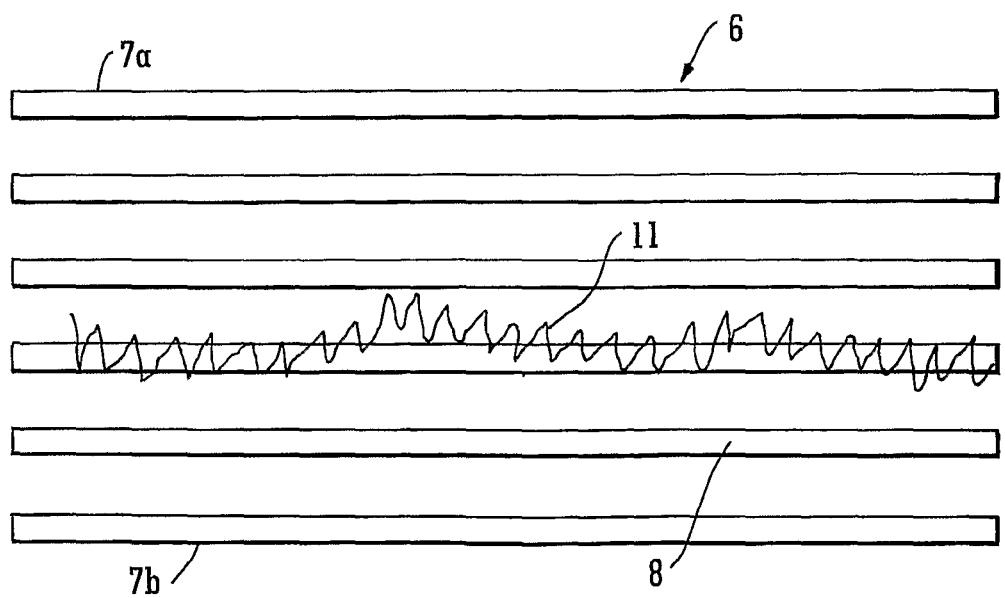
FIG. 9 shows the effect upon the trajectory of an ion by applying a DC compensation voltage to the lower electrode of the preferred device in order to compensate for the differential mobility induced drift of the ion towards the upper electrode.

FIG. 9 shows the result of a simulation wherein the same asymmetric waveform as was applied in the simulation described above in relation to FIG. 8 was applied to the upper electrode 7a of the preferred device 6 and wherein also a compensating DC voltage of −1.5 V was applied to the lower electrode 7b. The applied DC compensating voltage can be seen as having the effect of effectively cancelling out the net drift of the ion towards the upper electrode 7a. The ion is therefore now observed to be onwardly transmitted along and through the preferred device 6.

Figure 10:
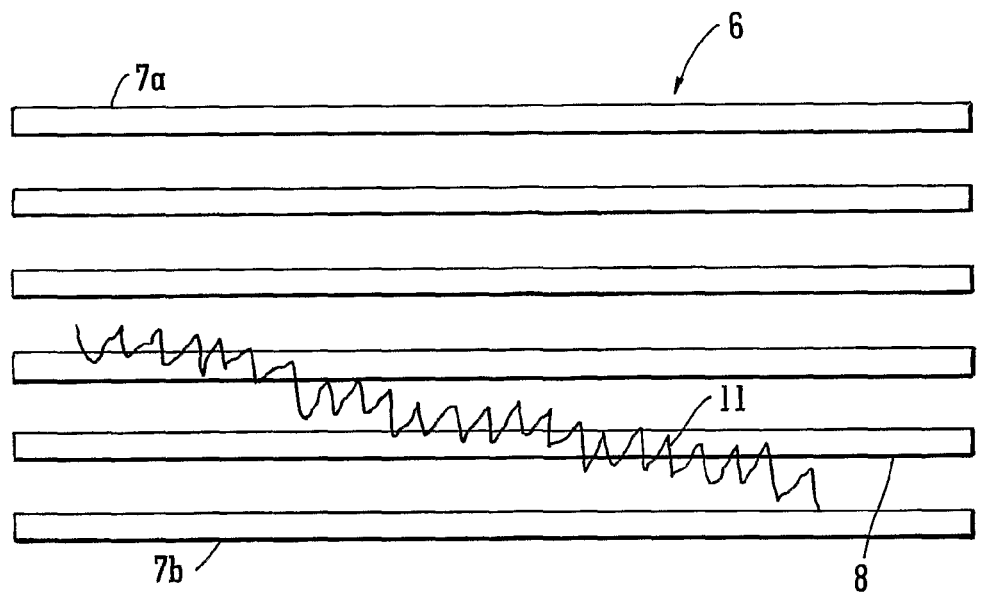
FIG. 10 shows the effect upon the trajectory of an ion if a DC compensation voltage is applied to the lower electrode which over compensates for the differential mobility induced drift of the ion towards the upper electrode.

FIG. 10 shows the result of a simulation wherein the compensating DC voltage applied to the lower electrode 7b was increased from −1.5 V to −2.0 V. It is apparent from FIG. 10 that the applied DC voltage now has the effect of over-correcting or over-compensating for the net drift of the ion towards the upper electrode 7a. The applied DC voltage actually causes the ion to drift now towards the opposite lower electrode 7b and ultimately to strike the lower electrode 7b.

Figure 11:
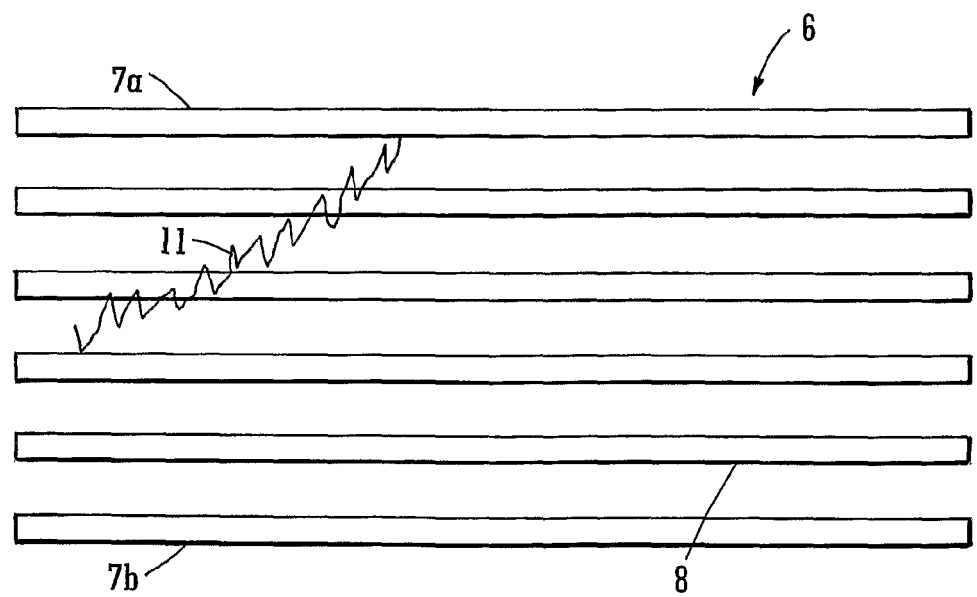
FIG. 11 shows the trajectory of an ion which was modelled as being subject to the same electric field conditions as described in relation to the embodiment described with reference to FIG. 8 but wherein the ion was modelled as having a larger cross-sectional area.

FIG. 11 shows the results of a simulation wherein the hard sphere interaction cross section used in the simulation model was increased from 200 to 300 Å². The parameter V was maintained at 7 V and the parameter T was maintained at 1 μs as with the simulations described above in relation to FIGS. 8-10. The asymmetric waveform was applied to the upper electrode 7a and the lower electrode 7b was maintained at 0 V DC.

It can be seen from comparing FIG. 11 with FIG. 8 that an ion having a larger cross-section will strike the upper electrode 7a sooner than an ion having a lower cross-section due to the ion having a reduced high field mobility if it has a larger interaction cross section.

Figure 12:
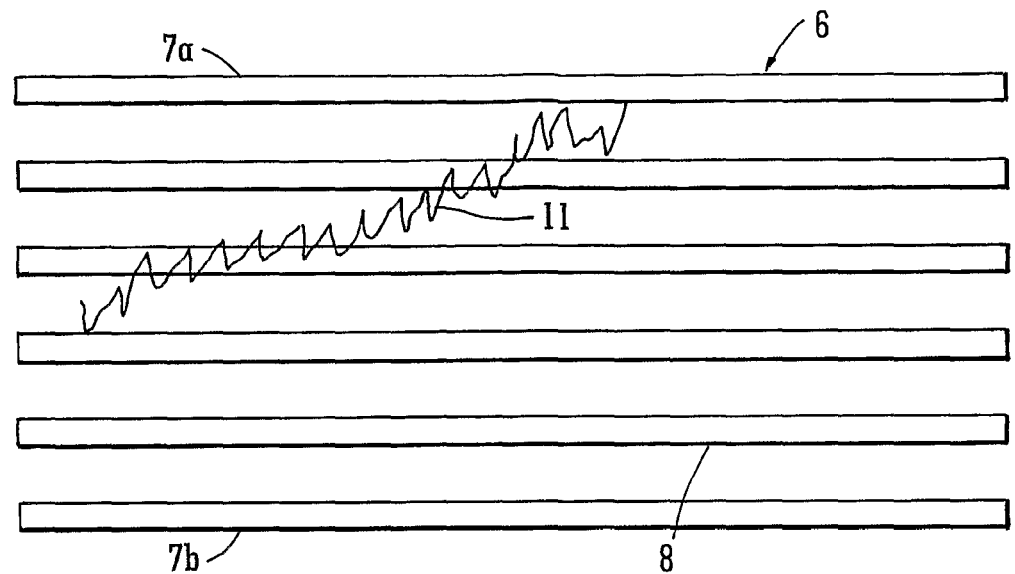
FIG. 12 shows that the trajectory of an ion towards the upper electrode is insufficiently compensated for if a DC compensation voltage having the same magnitude as the DC compensation voltage which as applied in the embodiment described with reference to FIG. 9 was applied to the lower electrode.

FIG. 12 shows the result of a simulation under the same conditions as for the simulation described and shown with relation to FIG. 11 except that a DC compensating voltage of −1.5 V DC was applied to the lower electrode 7b in a substantially similar manner to the simulation described above in relation to FIG. 9. However, it is apparent from FIG. 12 that the DC compensating voltage of −1.5V was insufficient to compensate for the drift of the ion towards the upper electrode 7a and was therefore insufficient to prevent the ion from striking the upper electrode 7a.

Figure 13:
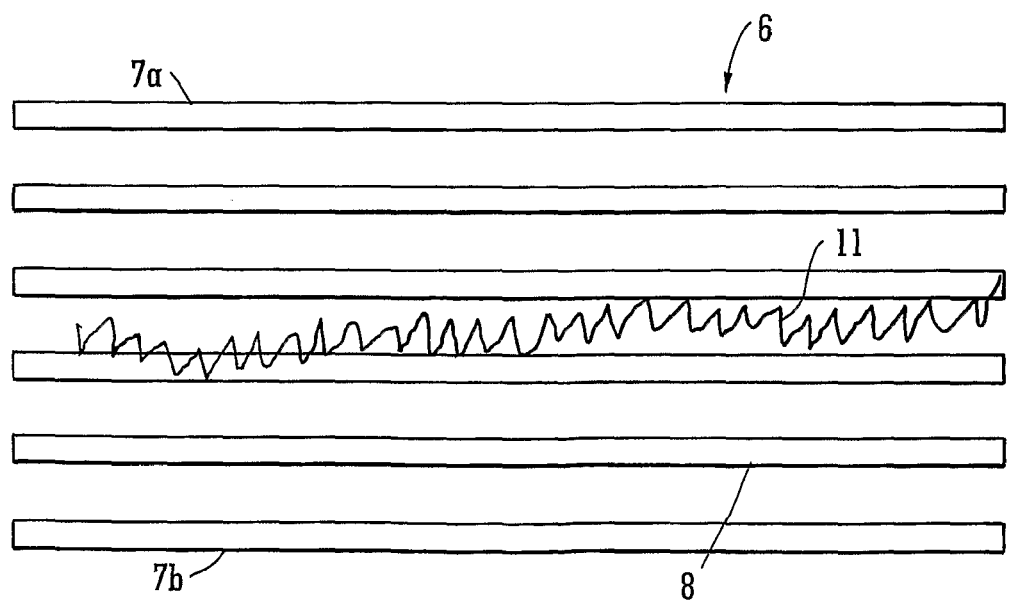
FIG. 13 shows how the trajectory of an ion may be modified or compensated for by applying the same magnitude DC compensation voltage which was applied in the embodiment described with reference to FIG. 10 to the lower electrode.

FIG. 13 shows the result of a simulation wherein the DC compensation voltage applied to the lower electrode 7b was increased from −1.5 V to −2 V. As can be seen from FIG. 13, increasing the DC compensation voltage to −2 V provided sufficient compensation for the net drift of the ion towards the upper electrode 7a such that the ion now passes along and through the preferred device 6 and is onwardly transmitted.

According to an embodiment of the present invention an ion mobility spectrum can be obtained by sweeping or progressively varying the DC compensating voltage which is preferably applied to the lower electrode 7b. Alternatively, the DC compensating voltage applied to the lower electrode 7b may be kept substantially constant so that only ions having a certain desired mobility are then onwardly transmitted by the preferred device 6.

The gas which preferably flows within and through the preferred device 6 may be due to an inflow of gas through a differentially pumped vacuum stage. Alternatively, the preferred device 6 may be enclosed in a housing or envelope and a gas may be supplied to the housing or envelope in order to raise the gas pressure within the preferred device 6 to an appropriate level. The housing or envelope may form a separate component of the mass spectrometer and may be contained or housed within a vacuum pumped chamber.

The ions entering the preferred device 6 preferably come from an ionisation source and are preferably entrained in a flow of gas. Alternatively, the ions may be created in a vacuum and/or may enter the preferred device 6 from a vacuum chamber.

A mass spectrometer including the preferred device 6 may preferably include an Electrospray, Atmospheric Pressure Chemical Ionisation, Atmospheric Pressure Photoionisation, MALDI, Inductively Coupled Plasma, Electron Impact or Chemical Ionisation ion source. According to other embodiments other ion sources may alternatively be provided.

Ions exiting the preferred device 6 may be detected directly by an ion detector. Alternatively, the ions exiting the preferred device 6 may be subjected to further analysis prior to detection by an ion detector. It is contemplated, for example, that according to an embodiment of the present invention the ions exiting the preferred device 6 may be subjected to mass spectrometric analysis, tandem mass spectrometry or further ion mobility spectrometry (or various combinations thereof).

The asymmetric waveform which is preferably applied to the upper and/or lower electrodes 7a,7b preferably has a rectangular waveform. However, according to other embodiments the asymmetric waveform may have a waveform other than rectangular. For example, the waveform may be curved.

The transport of ions through the preferred device 6 in a an axial direction (i.e. perpendicular to the mobility separation) was modelled in the embodiments shown and described above in relation to FIGS. 3-13 assuming that the gas flow velocity was kept.

According to a further embodiment instead of using a gas flow to predominantly cause ions to continue moving in an axial direction through and along the preferred device 6 one or more axial electric fields may also or alternatively be used in order to drive, force, propel or urge ions along the axial direction of the preferred device 6. Such an embodiment will be described now in more detail with reference to FIG. 14.

According to this embodiment the upper electrode and/or the lower electrode of the preferred device 6 may be axially segmented such that the upper electrode comprises an array of upper electrodes 12a-12e as shown in FIG. 14. Similarly, the lower electrode may also comprise an array of lower electrodes 13a-13e. The individual electrodes in the array of upper electrodes 12a-12e and the array of lower electrodes 13a-13e are preferably electrically isolated from one another. The device 6 as shown in FIG. 14 comprises an array of upper electrodes 12a-12e, four intermediate layers 8 of longitudinal electrodes and an array of lower electrodes 13a-13e.

According to one embodiment a constant linear or non-linear voltage gradient may preferably be provided along or maintained along at least a portion of the axial length of the preferred device 6.

According to another embodiment ions may be axially driven, propelled or urged along at least a portion of the axial length of the preferred device 6 by applying one or more transient DC voltages or potentials or one or more DC voltage or potential waveforms to the first array electrodes 12a-12e and/or to the second array of electrodes 13a-13e. The one or more transient DC voltages or potentials or one or more DC voltage or potential waveforms are preferably progressively applied to the array of upper electrodes 12a-12e and/or to the array of lower electrodes 13a-13e. The application of one or more transient DC voltages or potentials to the array of upper electrodes 12a-12e and/or to the array of lower electrodes 13a-13e preferably causes an electric field to be generated which ions can preferably surf or otherwise be propelled or urged along the length of the preferred device 6 by.

FIG. 15 shows a further embodiment comprising an array of seven upper electrodes 12a-12g, four intermediate layers 8 of electrodes and an array of seven lower electrodes 13a-13g. A transient DC voltage or potential is shown as being initially applied at a first time to a pair of first upper and lower electrodes 12a,13a. At a second later time the transient DC voltage is then applied to a pair of second upper and lower electrodes 12b,13b which are located downstream of the first upper and lower electrodes 12a,13a. The transient DC voltage is then progressively applied to subsequent pairs of electrodes e.g. to a pair of third upper and lower electrodes 12c, 13c, then to a pair of fourth upper and lower electrodes 12d, 13d, then to a pair of fifth upper and lower electrodes 12e,13e, then a pair of sixth upper and lower electrodes 12f,13f before finally being applied to a pair of seventh upper and lower electrodes 12g,13g.

The application of one or more transient DC voltages or potentials or one or more transient DC voltage or potential waveforms to the array of upper electrodes 12a-12g and to the array of lower electrodes 13a-13g is preferably such as to cause a series of axial potential wells to be formed or created within the preferred device 6. The axial potential wells are then preferably translated or otherwise moved along the axial length of the preferred device 6. The application of one or more transient DC voltages or potentials or one or more transient DC voltage or potential waveforms preferably enables the residence time of ions within the preferred device and hence in a region where they experience the effects of the orthogonally applied asymmetric field to be carefully controlled. This is a particularly advantageous feature of the preferred embodiment and enables the degree of ion mobility separation to be carefully controlled.

According to an embodiment of the present invention the velocity at which one or more axial potential wells are preferably translated along the length of the preferred device 6 can be varied or even temporarily stopped.

The ion transport volume within the preferred device 6 preferably has a substantially rectangular cross-section. However, other embodiments of the present invention are contemplated wherein the ion transport volume may have a cross-sectional form which is substantially non-rectangular. For example, it is contemplated that the cross-sectional form of the ion transport volume may vary along the axial length of the preferred device 6.

According to the preferred embodiment the ion confining volume within the preferred device 6 is preferably linear. However, according to other embodiments the preferred device 6 may have a non-linear or serpentine ion guiding path or region. A non-linear or serpentine ion guiding path or region may be provided in order to increase the overall length of the transport volume and, for example, to improve the differential separation of ions for a preferred device 6 having a certain given overall axial length.

Although the present invention has been described with reference to preferred embodiments, it will be understood by those skilled in the art that various changes in form and detail may be made to the particular embodiments discussed above without departing from the scope of the invention as set forth in the accompanying claims.

The invention claimed is:
1. A device comprising:
one or more first electrodes;
one or more second electrodes;
one or more layers of intermediate electrodes arranged generally or substantially in a plane in which ions travel in use, said one or more layers of intermediate electrodes being arranged between said one or more first electrodes and said one or more second electrodes, wherein each layer of intermediate electrodes comprises two or more longitudinal electrodes; and
first voltage means arranged and adapted to apply an asymmetric voltage waveform to said one or more first electrodes and/or to said one or more layers of intermediate electrodes and/or to said one or more second electrodes.

2. A device as claimed in claim 1, wherein said device is selected from the group consisting of: (i) a high field asymmetric waveform ion mobility separator or spectrometer; (ii) an ion mobility separator or spectrometer; (iii) a gas phase electrophoresis device; (iv) a differential ion mobility separator, spectrometer or device; (v) a Field Asymmetric Ion Mobility Spectrometry ("FAIMS") device; (vi) a gas phase ion separator or spectrometer; (vii) a device for separating ions according to their mobility; and (viii) a device for separating ions according to differences or changes of their ion mobility with electric field strength.

3. A device as claimed in claim 1, wherein said asymmetric voltage waveform comprises at least a first voltage component $V_{high}$ having a first peak amplitude and at least a second voltage component $V_{low}$ having a second peak amplitude, wherein said first peak amplitude is substantially different to said second peak amplitude.

4. A device as claimed in claim 3, wherein said first voltage component is applied or present for a first time period $T_{high}$ and wherein said second voltage component is applied or present for a second time period $T_{low}$.

5. A device as claimed in claim 1, further comprising second voltage means arranged and adapted to apply a DC compensation voltage to said one or more first electrodes and/or to said one or more layers of intermediate electrodes and/or to said one or more second electrodes.

6. A device as claimed in claim 1, wherein said one or more first electrodes comprises a first array of electrodes, having at least 2, 3, 4, 5, 6, 7, 8, 9, 10, 11, 12, 13, 14, 15, 16, 17, 18, 19, 20 or more than 20 electrodes.

7. A device as claimed in claim 6, further comprising further voltage means arranged and adapted to apply one or more voltages or potentials or one or more voltage or potential waveforms to said first array of electrodes in order to urge, propel, force or accelerate at least some ions through and/or along at least a portion of the axial length of said device.

8. A device as claimed in claim 1, wherein said one or more second electrodes comprises a second array of second electrodes having at least 2, 3, 4, 5, 6, 7, 8, 9, 10, 11, 12, 13, 14, 15, 16, 17, 18, 19, 20 or more than 20 electrodes.

9. A device as claimed in claim 8, further comprising further voltage means arranged and adapted to apply one or more voltages or potentials or one or more voltage or potential waveforms to said second array of electrodes in order to urge, propel, force or accelerate at least some ions through and/or along at least a portion of the axial length of said device.

10. A device as claimed in claim 1, wherein said one or more layers of intermediate electrodes comprise one or more layers of planar, plate or mesh electrodes.

11. A device as claimed in claim 1, wherein at least some or all of said longitudinal electrodes have a centre to centre separation in a width direction of the device selected from the group consisting of: (i)<1 mm; (ii) 1-2 mm; (iii) 2-3 mm; (iv) 3-4 mm; (v) 4-5 mm; (vi) 5-6 mm; (vii) 6-7 mm; (viii) 7-8 mm; (ix) 8-9 mm; (x) 9-10 mm; (xi) 10-11 mm; (xii) 11-12 mm; (xiii) 12-13 mm; (xiv) 13-14 mm; (xv) 14-15 mm; (xvi) 15-16 mm; (xvii) 16-17 mm; (xviii) 17-18 mm; (xix) 18-19 mm; (xx) 19-20 mm; and (xxi) >20 mm.

12. A device as claimed in claim 1, wherein said two or more longitudinal electrodes in a layer are substantially co-planar.

13. A device as claimed in claim 1, wherein said two or more longitudinal electrodes in a layer are supplied, in use, with substantially the same phase of a two-phase or multi-phase AC or RF voltage or signal.

14. A device as claimed in claim 1, wherein adjacent or neighbouring layers of longitudinal electrodes are supplied, in use, with substantially opposite or different phases of a two-phase or multi-phase AC or RF voltage or signal.

15. A device as claimed in claim 1, wherein at least 5%, 10%, 15%, 20%, 25%, 30%, 35%, 40%, 45%, 50%, 55%, 60%, 65%, 70%, 75%, 80%, 85%, 90%, 95% or 100% of said layers of intermediate electrodes are arranged substantially parallel to one another.

16. A device as claimed in claim 1, wherein said device is maintained, in use, at a pressure selected from the group consisting of: (i) <0.0001 mbar; (ii) <0.001 mbar; (iii) <0.01 mbar; (iv) <0.1 mbar; (v) <1 mbar; (vi) <10 mbar; (vii) <100 mbar; and (viii) <1000 mbar.

17. A device as claimed in claim 1, wherein said device is arranged and adapted to convert a substantially continuous beam of ions into a pulsed or discontinuous beam of ions.

18. A mass spectrometer comprising one or more devices as claimed in claim 1.

19. A method of separating ions comprising:
providing a device comprising one or more first electrodes, one or more second electrodes and one or more layers of intermediate electrodes arranged generally or substantially in the plane in which ions travel, said one or more layers of intermediate electrodes being arranged between said one or more first electrodes and said one or more second electrodes, wherein each layer of intermediate electrodes comprises two or more longitudinal electrodes; and
applying an asymmetric voltage waveform to said one or more first electrodes and/or said one or more layers of intermediate electrodes and/or said one or more second electrodes.

20. A method of mass spectrometry comprising a method as claimed in claim 19.

21. A device comprising:
one or more first electrodes;
one or more second electrodes; and
first voltage means arranged and adapted to apply an asymmetric voltage waveform to said one or more first electrodes and/or to said one or more second electrodes;
wherein said device is arranged and adapted to be maintained, in use, at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vii) 1-10 mbar; and (viii) 10-100 mbar.

22. A method of separating ions comprising:
providing a device comprising one or more first electrodes and one or more second electrodes;
applying an asymmetric voltage waveform to said one or more first electrodes and/or to said one or more second electrodes; and
maintaining said device at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vii) 1-10 mbar; and (viii) 10-100 mbar.

* * * * *